(12) United States Patent
Li

(10) Patent No.: US 9,649,230 B1
(45) Date of Patent: May 16, 2017

(54) INTELLIGENT INCONTINENCE MONITOR

(71) Applicant: Edward Li, San Diego, CA (US)

(72) Inventor: Edward Li, San Diego, CA (US)

( * ) Notice: Subject to any disclaimer, the term of this patent is extended or adjusted under 35 U.S.C. 154(b) by 0 days.

(21) Appl. No.: 15/239,674

(22) Filed: Aug. 17, 2016

(51) Int. Cl.
G08B 23/00 (2006.01)
A61F 13/42 (2006.01)

(52) U.S. Cl.
CPC ........ *A61F 13/42* (2013.01); *A61F 2013/424* (2013.01)

(58) Field of Classification Search
CPC ........ A61F 13/42; G08B 1/00; G06K 7/10366
USPC ................ 340/573.5, 604, 572.1, 539.1, 505
See application file for complete search history.

(56) References Cited

U.S. PATENT DOCUMENTS

| | | | | |
|---|---|---|---|---|
| 6,774,800 B2* | 8/2004 | Friedman | ............. | A61B 5/0002 340/572.5 |
| 6,876,303 B2 | 4/2005 | Reeder | | |
| 7,250,547 B1* | 7/2007 | Hofmeister | ............. | A61F 13/42 340/573.5 |
| 8,196,809 B2 | 6/2012 | Thorstensson | | |
| 8,237,572 B2 | 8/2012 | Clement | | |
| 8,502,684 B2 | 8/2013 | Bunza | | |
| 8,978,452 B2* | 3/2015 | Johnson | ................ | G01N 27/223 340/604 |
| 9,160,054 B2* | 10/2015 | Yu | ................ | H01Q 1/2225 |
| 2002/0145525 A1 | 10/2002 | Friedman | | |
| 2005/0046578 A1* | 3/2005 | Pires | ................ | A61F 13/42 340/573.5 |
| 2011/0309937 A1* | 12/2011 | Bunza | ................ | A61B 5/202 340/573.5 |
| 2014/0276504 A1* | 9/2014 | Heil | ................ | A61F 13/42 604/361 |
| 2014/0358099 A1* | 12/2014 | Durgin | ................ | A61F 13/42 604/361 |
| 2016/0267769 A1* | 9/2016 | Rokhsaz | ................ | G01N 1/00 |

* cited by examiner

*Primary Examiner* — Phung Nguyen
(74) *Attorney, Agent, or Firm* — Continuum Law; Robert P. Cogan

(57) ABSTRACT

A system for monitoring patient incontinence. A sensor module is positioned next to an impermeable layer of absorbent pad used for urinary or other incontinence. A wired embodiment has the sensor module wired to an external controller. In the wireless embodiment, a radio frequency identification (RFID) tag includes an antenna, moisture sensor, and radio frequency integrated circuit (RFIC). A rewritable memory is included in the RFIC to record identifying information associated with the patient. The identifying information is programmed in the RFID tag when it is in the range of an RFID writer. A controller-transceiver in this intelligent underpad monitor system provides excitation energy to operate the RFID tag. The controller-transceiver constantly interrogates the RFID tag to detect any incontinence alarm signal. When incontinence happens, the alarm signal is sent to the controller-transceiver along with user information in the RFID tag memory. In both wired and wired embodiments, the controller, which is a microprocessor, will process and screen the information as needed to communicate with the hospital information system.

22 Claims, 10 Drawing Sheets

INTELLIGENT INCONTINENCE MONITOR

FIELD

The present subject matter relates to an incontinence monitoring system utilizing a radio frequency identification (RFID) sensor with a programmable controller-transmitter for selectable control of the monitoring system.

BACKGROUND

Incontinence is a prevalent problem in many contexts. These contexts include nursing homes, acute care facilities, and intensive care units (ICUs). Incontinent patients have long been wrapped in diapers. Continued contact of the skin with body waste leads to Incontinence-Associated Dermatitis (IAD), known familiarly as "diaper rash." IAD can further develop into pressure ulcer (PU) and other secondary skin infections. According to *Changing Our Methods of Adult Incontinence Management to Decrease Skin Breakdown and Improve Patient Satisfaction*, 42nd Wound, Ostomy & Continence Nurses Society Conference, Jun. 12-16, 2010, 78% of acute-care hospitalized adult patients wearing diapers suffered from these conditions.

Major metropolitan hospitals are now banning diapers in favor of underpads because of the associated dermatological effects. Incontinence hospital patients are now placed on underpads while wearing open-back gowns. Underpads, which are multilayer pads, are preferable to diapers in that the contact area between waste and skin is minimized. Changing of an underpad is quite simple in comparison to changing a diaper.

Many approaches have been taken in the prior art to provide a sensor embedded in a multilayer absorbent article in order to indicate an incontinence event. In this manner, a patient can be attended to when there is a need rather than on a predetermined time schedule. Prior approaches have been embodied primarily in diapers. A number of these approaches utilize radio frequency (RF) resonance, and recently, radio frequency identification (RFID) incorporating advances in this technology. RFID is familiar to consumers as the technology that permits vehicle owners of RFID identification devices to bypass toll booths and enter secured garages without stopping. RFID offers added identification capability to RF resonance. User and usage data can now be recorded and retrieved wirelessly. Most RFID systems are continuously powered, not unlike cellular network systems in their quest for RFID tags or cell phones to be identified by the systems to fulfill requests for action. In view of recent government reports of continuous cell phone usage causing brain diseases, an RFID system that does not require continuous radio frequency query could mitigate this undesirable side effect.

An RFID tag primarily comprises an antenna. A passive tag is not powered; but when its antenna resonates with a signal generated by its mating controller-transceiver, the energy received powers on the tag integrated circuit to activate the tag. Passive RFID tags can be queried via a frequency with which the antenna is resonant. In response to excitation with a resonant frequency, the resonating antenna provides energy which can be stored in a capacitor, for example. Many variations of this arrangement are provided. Passive RFID tags are more convenient to use than active (powered) RFID tags. They do not depend on battery or external power to work and are suitable for reporting incontinence conditions wirelessly. Generally prior art using RFID tags do not take advantage of their "ID" capability, and only to identify tags for action sequencing purposes. Most use the tags because of their compactness and ease of use attributes. The RFID tags provide a binary output in effect. While the identification may reside in many bits of information, the end result is always confirmation of an authorized response, affirmative or not. The binary output is effective to provide acknowledgement to indicate a "wet" condition or absence of a wet condition.

United States Published Patent Application No. 20020145525 discloses a diaper comprising a plurality of RFID tags. Each of the RFID tags is coated with a dry electrolyte which enhances response to moisture. Each tag is also assigned a unique frequency. The sequence and relative response of tags to enquiring signals indicate position and moisture status. Because of the design complexity, implementation can be costly.

United States Published Patent Application No. 20140358099 discloses a system embedded in a diaper including first and second RFID tags respectively placed on an upper end and a lower end of a diaper with a moisture strip connected to both tags. This construction requires special fabrication to connect the RFID tags and the sensor. Standard, off-the-shelf components cannot be used.

U.S. Pat. No. 8,502,684 discloses a diaper with dissolvable conductive moisture sensor traces connected to an RFID tag antenna. Initial moisture contact will not completely dissolve the traces, and an antenna impedance change will indicate an initial moisture. A positive incontinence condition is indicated by complete dissolution of the traces, with the RFID antenna not functioning. Lack of response is indistinguishable from a complete failure. Special materials must be used for the conductive traces to avoid breaks during handling and in in situ wearing conditions U.S. Pat. No. 6,876,303 discloses a system for monitoring hospital personnel, a plurality of patient locations for patients and associated devices having a plurality of patient controls. Transmitters carried by each of a plurality of hospital personnel each periodically transmit a signal unique to that transmitter. The signal could indicate a patient or sensor triggered event alarm. A computer coupled to the associated devices is configured to respond to disable at least one of the patient controls while hospital personnel attend to the patient. This arrangement monitors hospital personnel and not patients nor their need status.

U.S. Pat. No. 8,237,572 and other patents, including U.S. Pat. No. 8,248,249 disclose an RFID tag and a system and method involving a plurality of RFID tags. Each RFID tag is attached to an object or to a structure or a person on which the presence of a predefined fluid is monitored. In a first state, absence of the monitored fluid, the tag is acting as a passive RFID tag and the information it holds can be read with a proximity RFID reader. This operation is performed when the RFID tag is attached to the object to be monitored. At this stage a table associating tag ID, object name and location may be built, and may be recorded so that information it contains is accessible by a control center. In a second state, whenever the monitored fluid appears on the tagged object, a fluid activated battery generates the electrical power which is used to power the RFID tag. The RFID tag then acts as an active RFID tag and starts to emit messages which can be received by a distant RFID reader. Alert messages include at least the tag ID but may comprise additional information like a name or a location. This method relies on activation of a battery by waste fluid. This is a nonconventional component.

U.S. Pat. No. 8,196,809 discloses a system including a reader and an absorbent article containing machine-readable information identifying the user associated with the absorbent article and the user's location. A computer uploads data from the reader and stores the identifying information. On retrieval of information from the computer memory, information concerning the absorbent article is automatically associated with the identity and location of a user of the absorbent article. This patent is only concerned with inventory of the absorbent article, and no live usage condition sensing is involved. This arrangement does not provide the benefit of monitoring the in situ status of the incontinence article as well as identification of its user and location.

SUMMARY

Briefly stated, in accordance with the present subject matter, there are provided a sensor module in the system for monitoring incontinence in one or more patients and for facilitating expeditious attention to patient needs in a home or institutional setting. The sensor is preferably, though not necessarily, placed on a flat substrate. Alternatively, the sensor can be placed in an underpad. In the healthcare context, an underpad is an absorbent pad made of one or more various materials and used for personal hygiene. Usually, the underpad is used in urinary incontinence. The present prevailing nursing practice is replacing a diaper with an underpad for incontinence care. Incontinence can be sensed by this system whether the patient is wearing a diaper or placed on an underpad. The absorbent layer holding the incontinence discharge in either diaper or underpad triggers the alarm condition that calls attention in a hospital situation. Because of the prevailing nursing practice, underpads and diapers will be synonymous in this discussion.

A sensor module is placed on a substrate of soft, pliable material such as silicone or rubber approved for use in hospitals. This sensor embedded substrate mat is placed beneath the underpad. Alternatively, the sensor module is placed on the waterproof layer of an underpad resulting in a custom made absorbent article. The sensor module comprises a passive radio frequency identification (RFID) tag to include an antenna, moisture sensor, and radio frequency integrated circuit (RFIC). A rewritable memory is included in the RFIC to record information on the incontinence underpad user. The identifying information is programmed in the RFID tag when it is in the range of an RFID writer. RFID writer can be the same RFID writer that hospitals use to encode patient RFID wristbands; or, alternatively, a dedicated unit. A controller-transceiver in this intelligent underpad monitor system provides excitation energy to operate the RFID tag. In the wireless embodiment the controller-transceiver constantly interrogates the RFID tag to detect any incontinence alarm signal. When incontinence happens, the alarm signal is sent to the controller-transceiver along with user information in the RFID tag memory. The alarm signal in the wired embodiment is similarly sent to its mating controller. The controller, which is a microprocessor in most applications, will process and screen the information as needed to communicate with the hospital information system. In complex installation requirements, a microcomputer may serve as the controller.

DETAILED DESCRIPTION

The present subject matter may be used in the context of diapers or underpads. However, diapers are now banned in most large hospitals and institutions because diaper use in adult patients is linked to diseases in the covered skin areas. In its stead, underpads are placed under the body to catch incontinence discharge. To further minimize skin diseases caused by prolonged contact, this underpad is designed to notify caregivers when incontinence occurs to require replacement. In a preferred embodiment, a thin, flexible substrate is incorporated with a wireless sensor. This thin substrate, in the shape of a book size mat, is placed beneath the patient's generic absorbent article, either an underpad or diaper. Alternatively, a wireless sensor is manufactured into the disposable underpad which is indistinguishable in use and handling compared to existing equivalent products. In wireless embodiments described below, an RFID sensor system is programmable with patient information for automated inventory, billing, location tracking, and other data driven medical or business functionalities. For a basic no-frills system, generic RFID tags costing pennies in volume can become a sufficient wireless sensor to be attached to a flexible mat sensor pad or be attached to a base layer of an underpad. Deployment of either version of this system will enable the host hospital to fulfill the twin Medicare and Affordable Care Act mandates of preventive and cost-effective care of incontinent patients.

Figure 1:
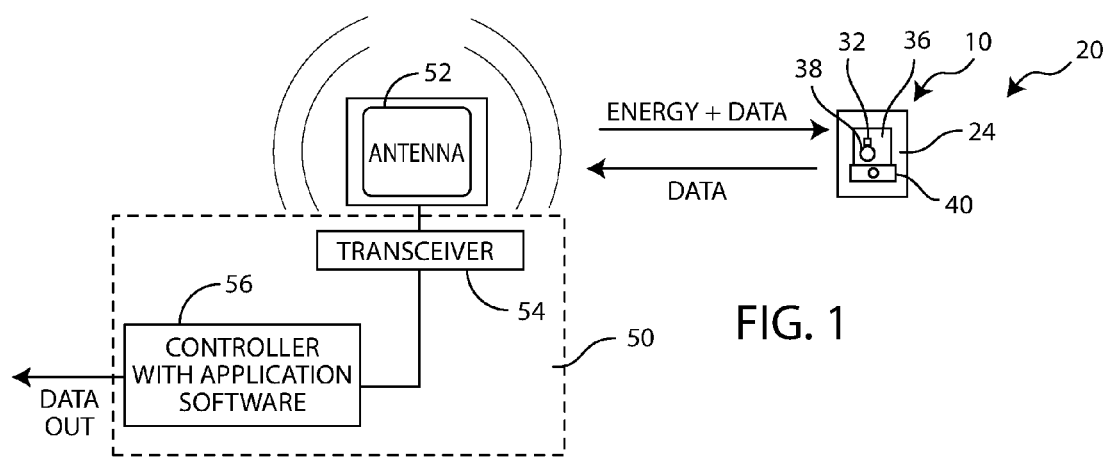
FIG. 1 is a diagrammatic representation of a RFID sensor system.

FIG. 1 is an illustration of the RFID embodiment of this Intelligent Incontinence Monitor system. This system diagram consists of RFID sensor module 10 on the right and Controller-Transceiver 50 on the left. Sensor module 10 comprises an RFID tag 20. In one preferred form, the RFID tag 20 is passive, i.e., it does not contain its own power source. RFID tags are substantially foil type two-dimensional electronic circuits used in near field communication (NFC). The physically predominant structure is an antenna 38. The antenna 38 is electrically connected to a very small integrated circuit, e.g., nominally 1 mm square or smaller, with read, write, and erase memory capability.

The RFID tag 20 includes circuit elements on a substrate 24. The substrate 24 commonly comprises a film. RFID tags have used other substrates as well. The RFID tag 20 further comprises an RFIC chip 32. The RFIC chip 32 includes a radio frequency modulation circuit element and a type of electrically erasable programmable memory (EEPROM) to provide further means for interaction. RFID tag 20 stores identifying data to distinguish one RFID tag 20 from another. RFIC chip 32 further comprises a microcontroller to direct the actions to be performed. Instead of a programmable microcontroller, the RFIC 32 can also be a set of logic gates that can intelligently perform dedicated functions, technically referred to as a "state machine". RFIC chip 32 directs sensor 20 to transmit data acquired and/or stored in the EEPROM.

A moisture sensor 36 has an electrical parameter that varies with moisture. The RFID tag 20 is coupled with the system by the sensor antenna 38. In some embodiments, the sensor 36 and sensor antenna 38 are distinct components. Alternatively, the sensor 36 and the sensor antenna 38 are combined.

RFID tag shapes can be round, square, or rectangular depending on antenna design and standardized RFID protocols chosen. The most compact form of RFID tag is a thin foil with an adhesive on one surface to bond to the host being tracked. There are broadly two types of RFID tags: active and passive. An "active" tag is supplied with electrical power, and can transmit its presence and unique information stored in its integrated circuit memory to a nearby mating transceiver-controller with which their respective antennas resonate. A passive tag is not externally powered. Energy received by the passive RFID sensor antenna 38 is coupled to storage elements 40, which could conveniently comprise a capacitor to provide power to activate a passive RFID tag.

FIG. 1 also discloses a controller-transceiver 50 including base antenna 52. The controller-transceiver 50 provides excitation signals having the same resonant frequency as the resonant frequency of the sensor antenna 38 to power on the RFIC chip 32. The same resonant frequency is used to denote that the resonant frequency of the antenna and the frequency transmitted by the transceiver 54 result in sufficient transfer of energy between RFID tag 20 and the transceiver 54 to allow operation as described herein. The activated RFID tag 20 then returns signals comprising sensor and user ID data held in its memory to be received by the controller-transceiver 50. The controller-transceiver 50 comprises a transceiver 54 and a controller 56 to respond to data thus received. The controller 56 is a processor uploaded with custom software to direct RF transmission to and receive from the RFID tag 20. It is also the interface to the notification network at a location such as a Nurses' Station and/or Hospital Network (FIG. 6) to receive an incontinence alarm signal. The alarm mechanism may be coupled to a detector 224 located at a hospital bed 130 (FIG. 3), a nurses' station 210 (FIG. 6), on a portable device carried by a hospital staff member, or at a remote location.

Figure 2A:
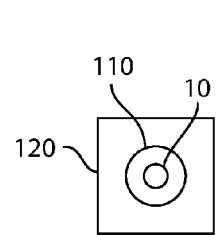
FIG. 2, consists of FIGS. 2A, 2B and 2C, FIGS. 2A and 2B being an illustration of a sensor built onto a mat or an underpad, and FIG. 2C being an illustration of a sensor module fixed to the outside of a moisture barrier layer.

FIG. 2A is an illustration of the RFID sensor module attached to a mat to be placed beneath an unmodified, generic underpad. The sensor module 10 is fixed to a flat, flexible substrate, a mat nominally made from sanitary polymer or rubber constitution at location 110. Location 110 is preferably set in a position intended to be placed in registration with an expected location for a patient's bodily waste, nominally in the center of a generic underpad 100.

Figure 2B:
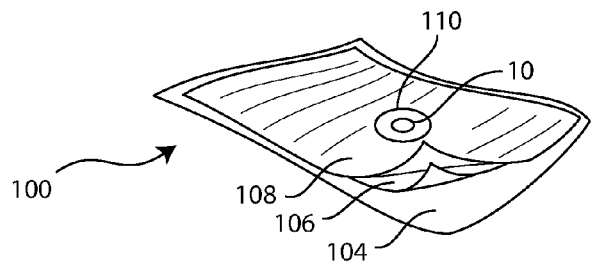

FIG. 2B is an illustration, partially broken away, of the sensor module 10 built into a custom made underpad 100. The underpad 100 is comprised of three layers. A first, moisture barrier layer 104 is an outer layer farthest away from the patient. The moisture barrier layer 104 may conveniently comprise a plastic sheet. A second central layer is an absorbent layer 106. In different embodiments the absorbent layer 106 may comprise paper pulp and/or polymer. A third, surface layer, which may also be referred to as a top layer, is a soft layer 108 which will contact the skin of a patient and mitigate sticking and enhance tactile feel. The soft layer 108 may comprise gauze netting. The underpad 100 is shown partially broken away to reveal a location 110 of the RFID tag 20. The sensor module 10 is fixed to the moisture barrier layer 104 at the location 110. The location 110 is preferably set in a position intended to be placed in registration with an expected location for a patient's bodily waste, nominally in the center of underpad 100.

Figure 2C:
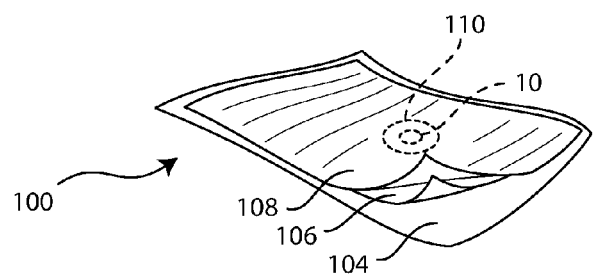

FIG. 2C is an illustration of a sensor module 10 fixed to the outside of the moisture barrier layer 104 at the location 110.

Figure 3:
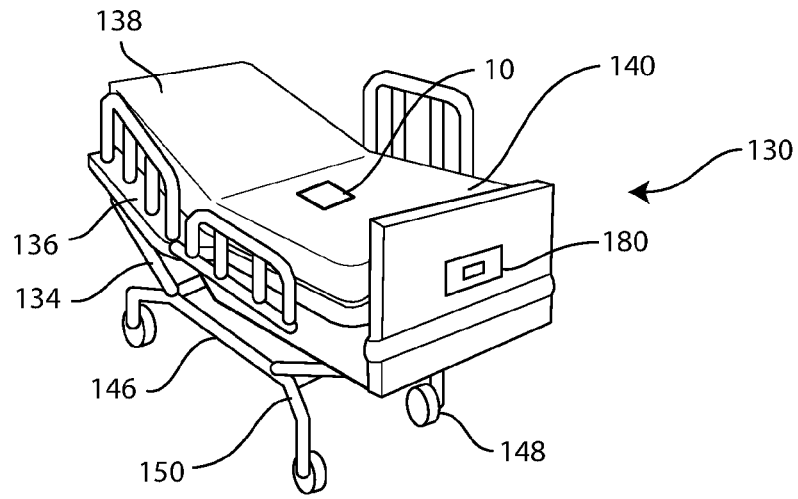
FIG. 3 is an illustration of a sensor placed on a mat or in an underpad, and on a hospital bed.

FIG. 3 is an illustration of a sensor module 10 used in conjunction with a hospital bed 130. The hospital bed 130 comprises a frame 134 including a base 136. A mattress 138 is mounted on the bed base 136. Bed linens 140 are used in conjunction with the mattress 138 in a conventional manner. The bed base 136 is operable by standard motors and controls to articulate the base 136. The hospital bed 130 may further comprise a bed control module 180. The bed control module 180 contains controls for the bed base 136 and for communication with a nursing station (not shown). The frame 134 is mounted on a carriage 146 which includes wheels 148 and a braking system 150.

The mat 120 (FIG. 2A) or underpad 100 (FIG. 2B) is placed on the mattress 138 on top of bed linen 140 positioned below an incontinent patient. Use of the sensor embedded mat 120 allows the use of generic, unmodified underpads while a sensor embedded underpad would not need the sensor embedded mat. The sensor location 110 (FIG. 2A or FIG. 2B) is chosen, preferably in a centered position, so that a patient's posterior will indent the pad. Consequently, urine will pool around the sensor module 10 due to gravity. The pooling will cause a greater amount of liquid to be present than in non-indented locations. In this manner, the sensor 20 can detect true wetness as opposed to minor leaks. Minor leaks will generally be distributed and should not trigger alarm conditions. The sensor embedded mat system offers the convenience of sensing incontinence without requiring underpads to be modified in any way. This sensor mat embodiment requires the use of Ultra High Frequency (UHF) RFID tags. UHF transmission is very sensitive to moisture, much more so than lower frequency MF (Medium Frequency), or VHF (Very High Frequency) radio waves, and UHF RFID tags are capable of sensing moisture without direct contact with the moisture from the underpad. Alternatively, UHF RFID tag module 10 can be attached to the outside of the underpad (FIG. 2C). When RFID sensor tags are attached to the inside of the underpad (FIG. 2B) either MF, VHF, or UHF types can be used.

Figure 4:
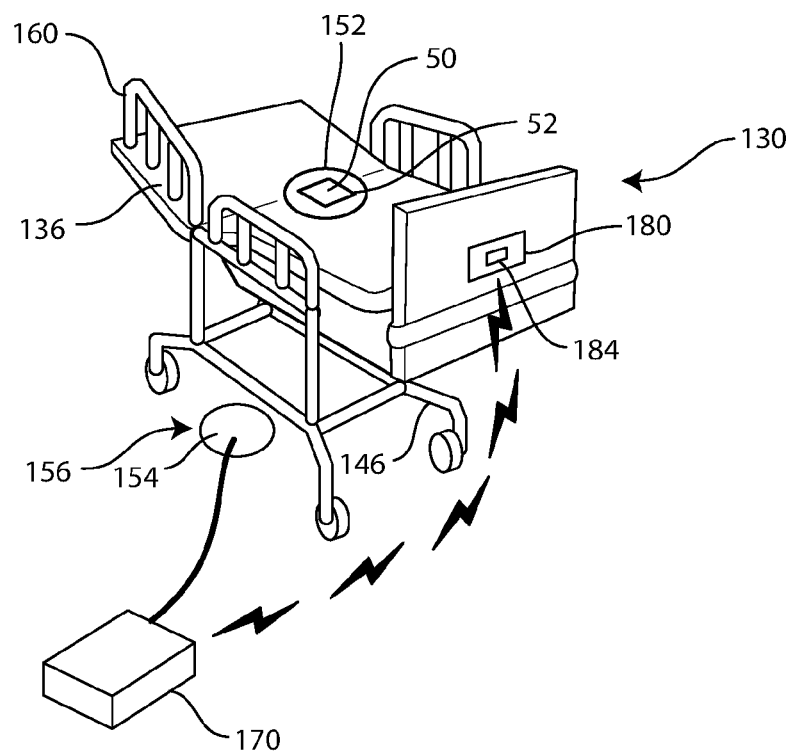
FIG. 4 is an illustration of controller installation on a hospital bed frame.

FIG. 4 is an illustration of the hospital bed 130 with the mattress 138 removed. The controller-transceiver 50 is placed on the bed base 136 at a location 152. The location 152 defines a horizontal position with which the sensor module 10 (FIG. 3) should be in substantial registration when placed on the mattress 138. Alternatively, the controller-transceiver 50 may be placed between the bed linen 140 and mattress 138 (FIG. 3). Optimal positioning places the controller-transceiver 50 less than 5 cm below the sensor. To activate the sensor module 10 at this optimal positioning, radiofrequency power on the order of milliwatts in some embodiments will be sufficient. In an embodiment in which the controller-transceiver 50 is placed under the mattress in position 152, higher excitation power is required. Communication distance between sensor module 10 and the controller-transceiver 50 is a function of a fixed ratio of vector distance and RF power. The controller-transceiver is programmed to automatically adjust the power level to a threshold power level just below being triggered by the effects of incontinence. Where the controller-transceiver 50 is coupled to a host hospital information system 220 (FIG. 6), outputs from sensor module 10 may be formatted to conform to a protocol used by the host hospital information system 220, as programmed through software in and directed by controller 56 (FIG. 1).

Figure 6:
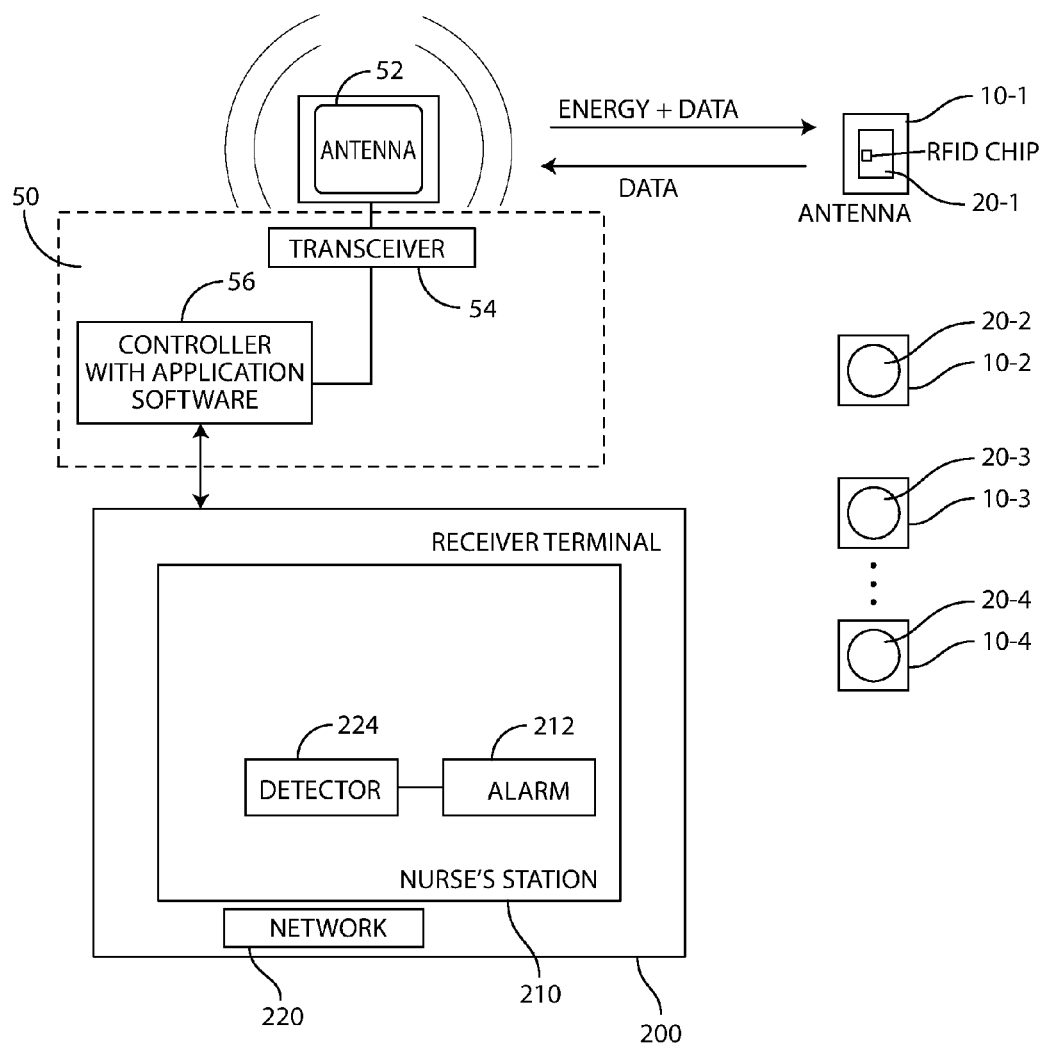
FIG. 6 is a diagrammatic representation of a hospital incontinence monitoring system.

Alternatively, a higher RF power controller-transceiver 50 may be positioned at a location 154 on a floor 156 in registration with the location 152. In further alternative embodiments, depending on RF power output, the controller-transceiver 50 may be placed on a bed carriage 146, hung on the wall 160 of a hospital, or be placed in a nurses' station 210 (FIG. 6). Power for controller-transceiver 50 can be tapped from a wall outlet or more conveniently, from the bed control module 180. The controller-transceiver 50 may be coupled to receive and forward signals from one or a plurality of sensor modules 10 because each embedded RFID tag 20 is uniquely identifiable.

The controller-transceiver 50 transmits and receives radio frequency to and from the sensor module 10. The controller 56 is responsible for processing and verifying the "wet" condition reported by sensor module 10, then send the alarm signal to a designated receiving station using any required protocol and/or encryption. This receiving station can be accessed from hard wiring controller 56 to a bed control module 180 and from there to the nurses' station or hospital trunk information network (FIG. 6). Alternatively, controller-transceiver 50 may be coupled to a Wi-Fi broadcast module 170 (FIG. 4). The hospital bed control module 180 also may include a Wi-Fi hub 184 to receive signals from the Wi-Fi broadcast module 170. In either a wired or wireless embodiment, the bed control module 180 will send an alarm signal and other data e.g., identification, finer-grain sensor information, to nurses, doctors, relatives or log directly into patient's medical and/or billing records.

Figure 5:
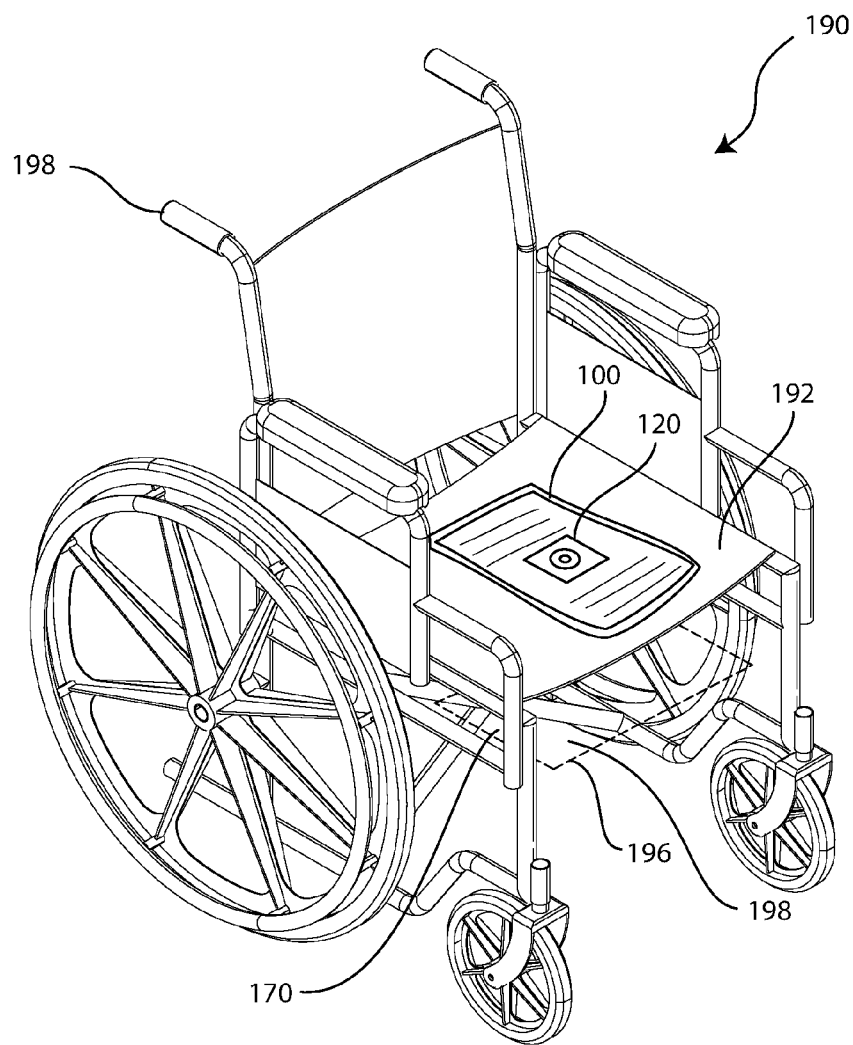
FIG. 5 illustrates alternative installation embodiments in a wheelchair.

FIG. 5 illustrates an alternative embodiment installed in a wheelchair 190. The mat 120 or underpad 100 is placed on a seat 192. As with the hospital bed 130, alternate positions for the controller-transceiver 50 may be selected. The controller-transceiver 50 could, for example, be fixed to a lower surface of the seat 192. Alternatively, the controller-transceiver 50 could be placed on a shelf 196 holding a battery 198 in a wheelchair 190. In this case, Wi-Fi broadcaster 170 (FIG. 4) will also be located under the chair and connected to battery 198.

FIG. 6 is a block diagram of an embodiment of an RFID based intelligent incontinence monitoring system. There is a plurality of sensor modules 10 numbered 10-1, 10-2, 10-3 through 10-n, where n is an integer. Each sensor module 10 is associated with a patient in a venue such as a hospital ward. The controller-transceiver 50 is positioned close to the mat 120 or underpad 100. The RFID tag 20 in the mat 120 or underpad 100, and controller-transceiver 50 are both tuned to the same radio frequency to couple to one another via resonance. A high powered controller-transceiver 50 is directed by controller 56 to transmit radio frequency energy to activate the RFID tag 20 or to activate a plurality of tag 20s, and then to receive and process the requested information coming back. Recently, mobile phone RF radiation is tied to cancer, and reducing continuous exposure may mitigate this condition. Controller 56 can be programmed to pulse RF radiation at fixed intervals and duration to reduce radiation dosage received by all within the range of controller-transceiver 50 transmission.

One of the primary functions of the controller 56 is to output a signal to trigger an incontinence alarm in an alarm circuit 212. There is "anti-collision" circuitry built into controller 56 in case more than one sensor module broadcasts alarm signals on the same frequency simultaneously. The alarm circuit 212 may be configured in one of a number of selected ways. For example, an on-off signal may be provided to a local alarm, visual or aural, or to an alarm switch common in hospital beds to send a bed occupancy alarm to the nurses' station 210. The Wi-Fi hub 184 (FIG. 4) is coupled to relay signals transmitted from the Wi-Fi broadcast module 170. Alternatively, a Wi-Fi alarm signal may be sent by Wi-Fi hub 184 included in the hospital bed control module 180 to a preselected receiver terminal 200.

The receiver terminal 200 may include one or more forms of apparatus that receive data from the sensor modules 10 via controller 56 to process and/or display that data. The receiver terminal 200 may comprise a conventional nurse station 210 with displays and alarms corresponding to each of a plurality of hospital rooms. Another embodiment comprises an interface to a trunk hospital information system 220. The outputs from controller-transceivers 50 and processed through controller 56 are transformed by appropriate, programmable software for connection to the hospital information network 220 configured protocols and/or encryption. For example, the trunk hospital information system 220 may comprise an interface in which data from the controller 56 is packaged into appropriate packets for transmission to local processors or computer terminals in the 220 network. Alternatively, controller 56 can also be programmed to pre-packetize the data without assistance from any hospital computers.

Figure 7:
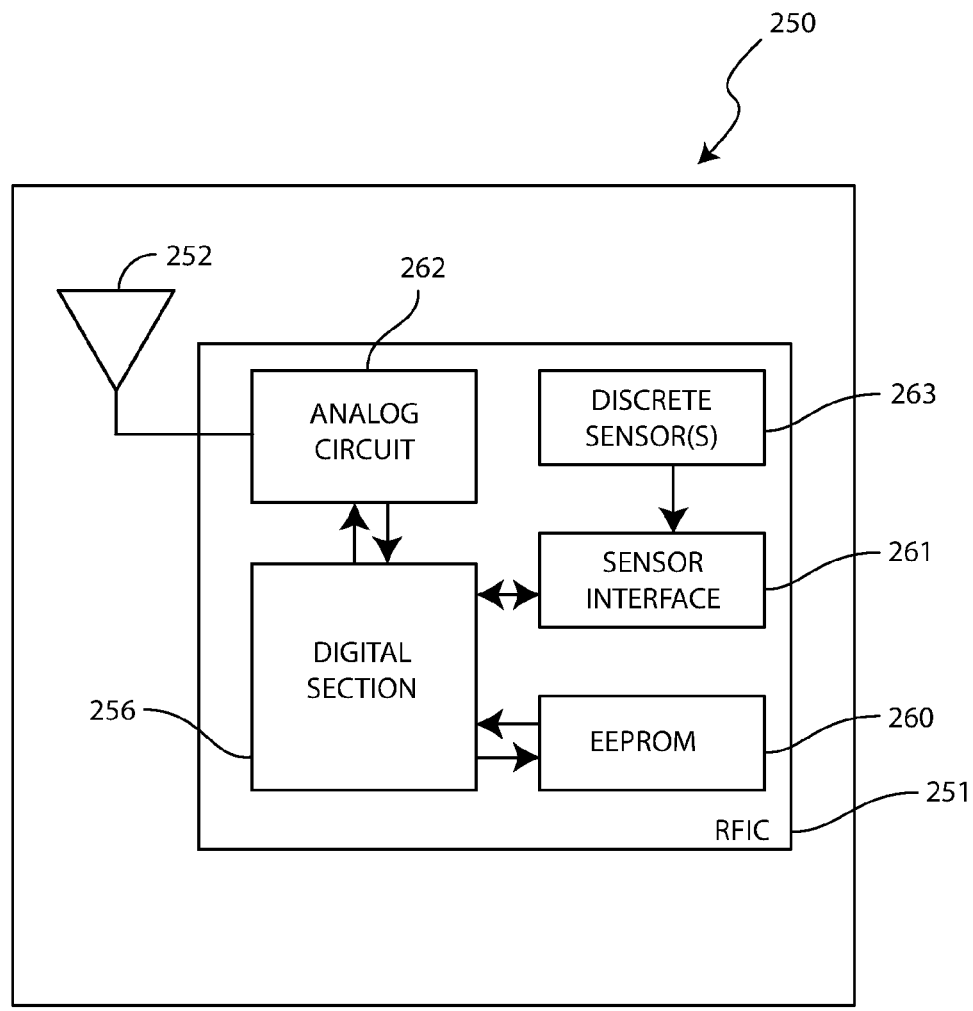
FIGS. 7 and 8 are block diagrams of a more advanced RFID system embodiment.

FIG. 7 is block diagram of another embodiment of the RFID sensor module 10. This embodiment features a more feature-rich RFID tag 250 and comprises an RFIC 251, which may be similar to the RFIC 20 (FIG. 1). This RFIC 251 incorporates analog circuitry 262 with RF energy harvesting and signal modulation/demodulation. The digital circuitry 256 is robust with more processing power, cooperating with an EEPROM 260 to handle the demands of sensor interface 261. One or more discrete sensors 263 can be incorporated in RFID tag 250 when coupled to sensor interface 261. The added discrete sensors can be used independently or incorporated in an embodiment of the antenna 252 in which signal output varies with moisture between conductors in the antenna 252. The antenna 252 provides similar functionality as the sensor antenna 38 in FIG. 1 as a moisture sensor in the sensor embedded underpad embodiment. Added discrete sensors can include another moisture sensor to provide finer-grain moisture data. Temperature, pH, pressure, gas concentration, or similar environmental parameters could also be provided. Extra inputs from these added sensors are processed in digital section 256 and data coded to EEPROM 260 to be retransmitted out to the more robust Controller-Transceiver 300 in FIG. 8. EEPROM 260 will also be programmed with user and hospital-related tracking data using an RFID writer.

Figure 8:
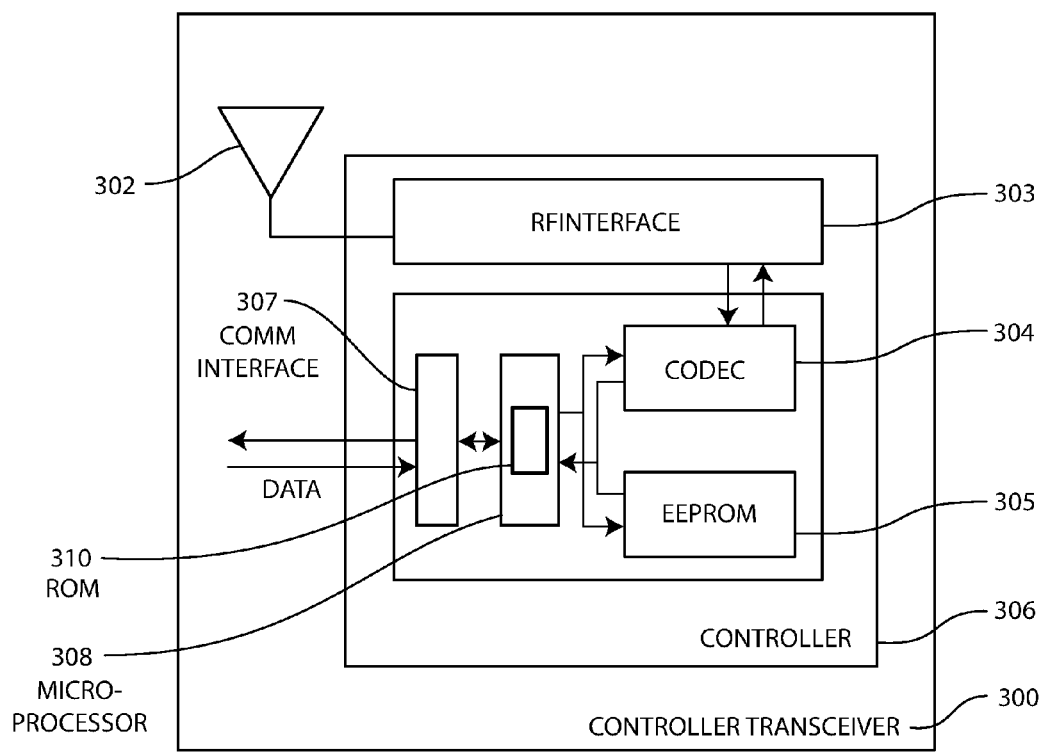

FIG. 8 is a block diagram of a matching feature-rich controller-transceiver embodiment comprising a controller-transceiver 300 having an antenna 302 and a controller 306 for interacting with the RFID tag 250 of FIG. 7. Components include an RF Interface 303 and communications interface 307. The system further comprises a Codec 304 and an EEPROM 305 each cooperating with a microprocessor 308. Software is loaded into microprocessor 308 to direct the performance of selected functions under preselected conditions. Features and capabilities of microprocessor 308 can be custom-matched to satisfy demanding field use requirements. Alternatively, firmware may be factory programmed into a read only memory (ROM) 310 residing in each microprocessor 308. Microprocessor 308 can compare preselected parameters to sensor acquired data to set alarm condition(s). Preselected conditions comprise moisture levels, levels of other parameters if measured, or whether the patient is on a bed, chair, or wheelchair, and location of underpad inside the hospital or institution. This latter location tracking can be possible with a capable microprocessor to triangulate the target sensor module location along with other non-targeted sensor modules located elsewhere on the hospital ward or floor. Protocol tailoring may include data encryption-decryption and detailed traceability of information so RFID controller 300 may adapt to any hospital information system requirement. Depending on preference, controller-transceiver 300 can even act as a distributed data terminal to output formatted data to a display or printer. Additionally, the controller in controller-transceiver 300 can direct transceiver 300 to cycle RF power at preset intervals to conform to probable future RF radiation dosage limits set for hospitals. This is possible because incontinence events are not as time critical as heart attacks.

Figure 9:
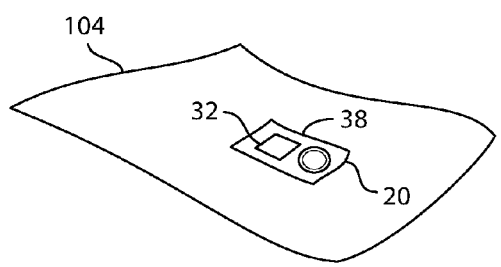
FIGS. 9 through 12 each illustrate one embodiment of a sensor.
Figure 10:
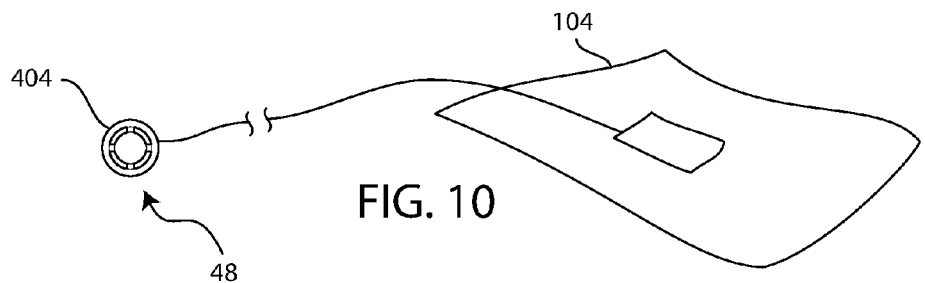
Figure 11:
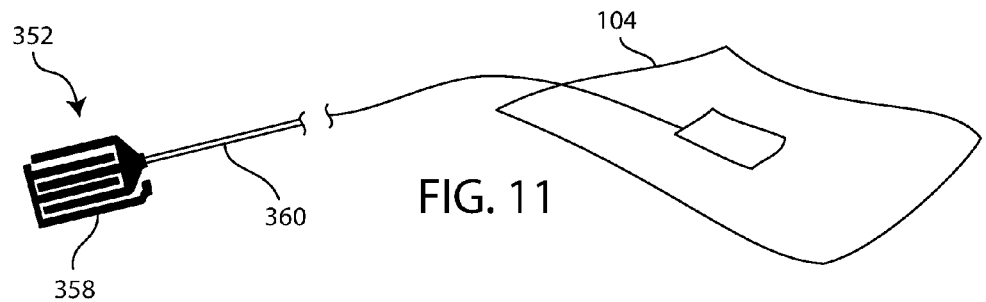
Figure 12:
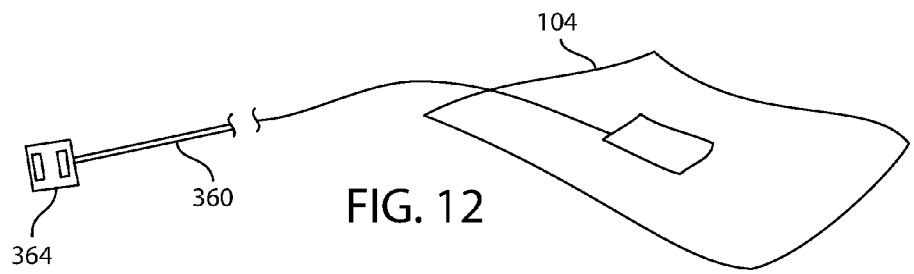

FIGS. 9 through 14 each illustrate one sensor module embodiment for embedding in underpads. Choice of which embodiment to deploy depends on user requirements and budget. FIGS. 9, 10, 13 14 are wireless embodiments, while FIGS. 11 and 12 are wired systems. Each of these embodiments will output a binary (on/off) alarm signal which can be forwarded or be used as a local visual or aural alarm or can be routed to a Wi-Fi network to reach designated notification devices.

FIG. 9 illustrates a typical passive RFID tag 20 comprising the RFIC 32 and the sensor antenna 38. The sensor antenna 38 can sense moisture, or a dedicated moisture sensor can be additionally designed in. This is the embedded underpad embodiment embraced in the basic RFID tag 20 discussed in detail in FIGS. 1-6. An antenna 38 with RFIC chip 32 in a very compact foil circuit can act as moisture sensor or the RFIC chip 32 can separately accept information from a dedicated moisture sensor added in the circuit if so designed. The RFID tag 20 resonates with an RF signal sent by the transceiver 54 tuned to the same frequency. Thus powered, the RFID tag 20 sends data as commanded by the controller 56 (FIG. 1). Moisture affects radio frequency transmission; also detunes the antenna 38. An alarm condition is triggered by information received that is indicative of moisture. Coded information in the RFID tag 20 can further supply moisture saturation status, tag identification, and additional parameters if included in the structure of the RFID tag 20. Software in the controller 56 manages communication between RFID tag 20 and the transceiver 54 including coding corresponding to the operation described above. Protocol/frequency choice is a function of system design and installation requirements.

In the embedded underpad embodiment of FIG. 10, an inductor comprising, for example, a thin-foil passive RF coil 48 is mounted circuit side up to the attached moisture barrier layer 104. The sensor can be the same as sensor module 10 in FIG. 1, except that implementation is bare-bone. Here the antenna coil 48 becomes a low cost RF coil 404 which resonates with a matching RFID reader used as a detector. Magnetic reluctance of the RF coil 48 changes with moisture. The change in reluctance activates the alarm condition. The goal of this embodiment is to sense an incontinent event without any need of patient identification. Each sensor module 10-equipped underpad 100 may be mass produced. No user ID information is needed, and no programming is needed to prepare the underpad for use. RFID readers generally trigger a built in binary signal (alarm) when a tag is detected. Only a minor logic inversion modification is needed to indicate that the sensor stopped transmission because the RFID antenna, the RF coil 48, is saturated.

FIG. 11 illustrates a wired embedded underpad embodiment. A conductive grid 358 comprises a sensor 352. A wire pigtail 360 is hard wired to the conductive grid 358 for connection to a threshold circuit which is AC or DC powered. The threshold circuit senses changes in conduction or capacitance to trigger an alarm signal. Resistance and capacitance each vary with moisture. The conductive grid 358 can be conductive ink printed on the underpad lining 104 or be a discrete small metal grid adhered to the same lining. Alarm signals can easily be ported to a Wi-Fi network using a USB or Bluetooth mobile phone connection.

FIG. 12 is another embedded underpad embodiment of a wired sensor system. Here a commercial, off-the-shelf, moisture sensor 364 with a wire pigtail 360 is connected to a suitable detector module which senses moisture and activates an alarm signal. The moisture sensor 364 may sense moisture, temperature, pressure, conductance, capacitance, or a combination thereof. The detector (not shown) is designed to work with the type of commercial moisture sensor installed on the underpad lining 104. Again, alarm signals can easily be ported to a Wi-Fi network via a USB or Bluetooth connection to a mobile phone, for example.

Figure 13:
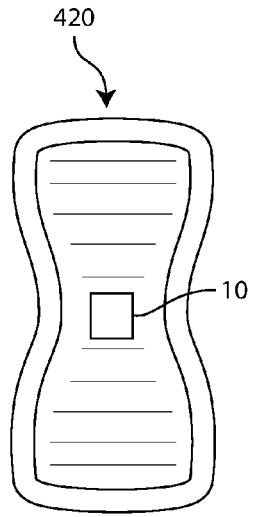
FIGS. 13 & 14 are embodiments of RFID sensor uses other than on an underpad.
Figure 14:
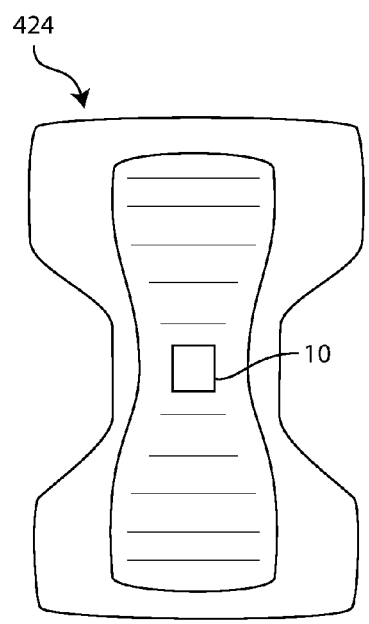

FIGS. 13 and 14 respectively illustrate an RFID sensor module 10 (FIGS. 1 & 6) in an infant diaper 420 and a toddler diaper 424. In each embodiment, the sensor module 10 is positioned at the user's crotch. Sensor modules can be wired or wireless. Wireless RFID sensor tags using any available frequencies are embedded inside the moisture proof liner to receive direct moisture contact while the UHF (and above) types can be attached on the outside of the diaper similar to FIG. 2C. Any of the matching controller-transceivers described previously can be used. These embodiments are particularly suited for home use. The present invention is not limited to use in an underpad. It is applicable to any general sanitary use absorbent articles including, but not limited to all diapers, undergarments and pads.

Figure 15:
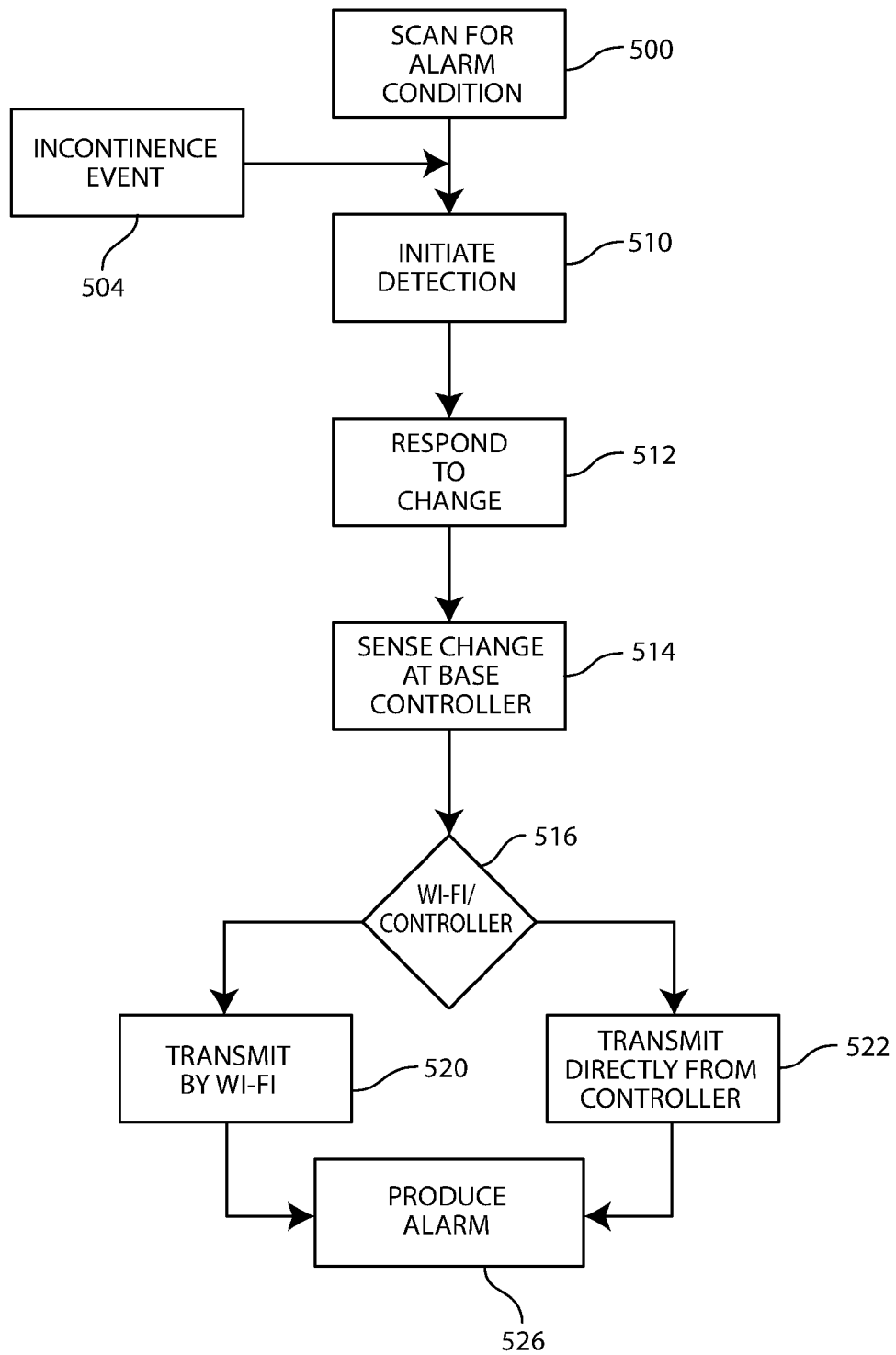
FIG. 15 is a flow diagram of the dynamic operation of the present system.

FIG. 15 is a flowchart illustrating dynamic operation of the present RFID system. At block 500, the controller-transceiver 50 starts scanning for alarm conditions from sensor mat or sensor embedded underpads on a continuous or intermittent operational mode. Intermittent operation mode is a user option to allay possible future radio frequency total dosage allowed in enclosed public spaces such as hospitals and care institutions. Previously, identification code is written in RFID tag 20 (FIG. 1) by a suitable RFID writer and the mat or sensor embedded underpad is deployed in situ. At block 504, an incontinence event starts. The initiation of an incontinence event is random in that it is aperiodic and subject to a wide variety of variables. At block 510, detection of an incontinence event is initiated. In a wireless embodiment, the controller-transceiver 50 continues to interrogate the RFID tag 20 at block 500. Electrical characteristics of the RFID tag 20 change with moisture, and an alarm is initiated. In a wired embodiment, a potential is applied across the wired pigtail 360 described in FIGS. 11 and 12. The potential may be steady state. At block 512, a response is generated to the initiation of the incontinence event. This response, in the case of the basic embodiment in FIG. 1, is a change in sensor 36 impedance. At block 514, the change in output of the RFID tag 20 is sensed by the controller-transceiver 50 (FIG. 1). Block 516 illustrates the option illustrated in FIG. 4 of providing the incontinence signal directly from the controller 56 or via the Wi-Fi transmitter 170 (FIGS. 4-5). The signal may be transmitted by Wi-Fi at block 520. The signal may be transmitted directly from controller-transmitter 50 at block 522. The incontinence signal is broadcast to the hospital information system at block 526 via controller 56 to trunk hospital information network 220 (FIG. 6).

Figure 16:
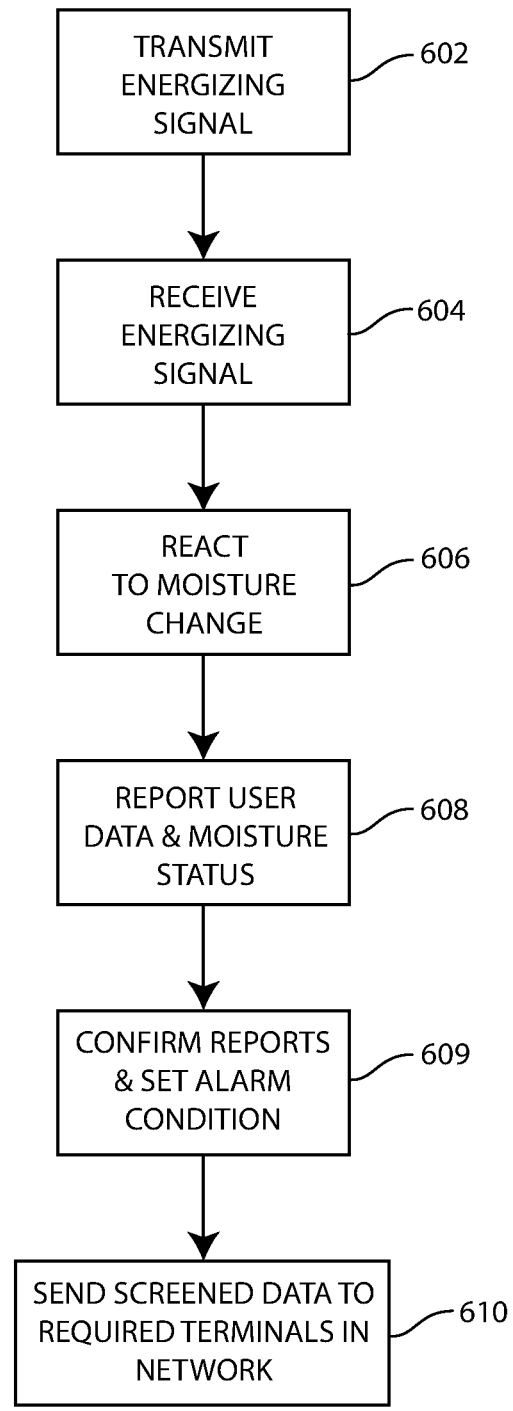
FIG. 16 is a flow diagram of the successive operation of the present system.

FIG. 16 is a flowchart representing a non-transitory program to illustrate coordination of transceiver 54 and controller 56 (FIGS. 1 & 6) in relation to changes in the RFID tag 20. Similar execution steps would happen in the higher functioning embodiment system of FIGS. 7 and 8. At block 602 an energizing signal is provided from the controller-transceiver 50. At block 604 the RFID tag 20 receives energy from a transmitted signal at a resonant frequency. At block 606 the sensor module 10 reacts to moisture change. At block 608 the sensor tag 20 transmits moisture status along with all hospital user and patient user data to controller-transceiver 50 (FIGS. 1 & 6) or controller-transceiver 300 (FIG. 8). At block 609 controller 56 acknowledges receipt of alarm and data and compares sensed signals to reference levels stored in its microcontroller as well as where to forward the alarm signal; what type of data to be forwarded to each station in the hospital information system network or networks, and will process the data to the information system network required protocol and/or security format. The amount of decision and processing is dependent on installation specification and may require more advanced controller module 306 as illustrated in the FIG. 8 embodiment. At block 610 controller-transceiver 300 sends data and/or packets out to the hospital information system network. Inside the hospital information system network, the specific attendant nurse needs to receive each patient's incontinence alarm while the hospital Patient Records Department may need to have the alarm occurrence and frequency logged into the patient's hospital record for medical and/or service audit use. The hospital Accounting Department may also want a record of each underpad used for billing purposes. There could be more notifications required and each may require it owns protocol. The controller can be scaled, selected, and upgraded as necessary. The proposed system is both versatile and flexible.

The invention claimed is:

1. An incontinence monitoring system comprising:
   a moisture sensor module, said sensor module comprising;
   a condition-responsive sensor coupled for producing acquired sensor data;
   an RFID tag comprising an antenna having a resonant frequency;
   said RFID tag further comprising a programmable memory, a microprocessor coupled for receiving the acquired sensor data and for comparing acquired sensor data to at least one preselected threshold level;
   a controller coupled to receive inputs indicative of at least an identification to program into the RFID tag;
   said controller and said RFID tag comprising components to provide power to communicate across a preselected vector distance; and
   a transceiver, said transceiver being coupled to said controller and wherein said controller is programmable to power said transceiver to transmit intermittently, whereby radiation dosage from said transceiver is maintained below a preselected limit.

2. A system according to claim 1 wherein said RFID tag comprises a UHF RFID Tag and wherein said transceiver is powered at a level sufficient to communicate with said UHF RFID tag sensor module over a preselected vector distance and in the presence of absorption of UHF signals by incontinence moisture.

3. A system according to claim 2 wherein said controller is responsive to presence of a comparison signal from said RFID tag to generate an alarm signal.

4. A system according to claim 3 wherein said controller comprises an alarm indicator responsive to the alarm signal at a remote location.

5. A system according to claim 4 further comprising a Wi-Fi broadcast module located at the preselected distance from said controller-transceiver and broadcasting signals to the remote location.

6. A system according to claim 5 wherein said remote location comprises at least one member of a group consisting of a nurses' station, information system network, and an individual interacting with the system.

7. A method for monitoring incontinence comprising:
   providing a sensor module, the sensor module comprising a UHF RFID tag and receiving a signal resonant with an antenna of the sensor module, the sensor module being placed to respond to moisture in an absorbent article, the sensor module being placed outside of the absorbent article;
   placing the sensor module in a position with respect to an individual to respond to moisture released by the individual;
   receiving a condition-responsive sensor signal from the sensor; and
   providing a programmed microprocessor containing a set of data including identification associated with the RFID tag and a threshold level indicative of an alarm status of the sensor condition, said condition-responsive sensor comprises a moisture sensor and wherein providing said RFID tag comprises providing said UHF RFID tag and positioning said UHF RFID tag within a preselected distance of moisture in the absorbent article, wherein UHF radio waves are particularly absorbed by moisture, and whereby UHF radio wave retransmission is proportionally degraded.

8. A method according to claim 7 comprising providing a controller-transceiver providing a signal having a frequency for activating the sensor module and querying the sensor module with the signal at powered intervals directed by a controller, whereby radiation dosage from said transceiver is maintained below a preselected industrial safety limit.

9. A method according to claim 8 comprising sensing an alarm condition wherein a sensor signal is detected as being anomalous and transmitting an alarm signal indicative of the alarm condition.

10. A method according to claim 9 wherein the step of transmitting a signal indicative of the alarm condition comprises transmitting the alarm signal to at least one member of a group consisting of a nurses' station, information system network, and an individual interacting with the system.

11. A RFID tag based incontinence monitoring system comprising:
    a controller-transceiver coupled to generate MF/VHF/UHF Band RF signal;
    a moisture sensor and antenna, said antenna tuned to a radio signal in the MF/VHF Band is the contacting moisture sensor in a wireless embodiment;

said moisture sensor and antenna, said antenna being tuned to said radio signal in the UHF Band where the UHF signal is the non-contacting moisture sensor in said wireless embodiment;

a UHF RFID tag module in the form of a passive UHF RFID tag and tuned to generate a return signal in response to an excitation signal;

said controller-transceiver providing said excitation signal to power generation of said return signal by said UHF RFID tag in the presence of absorption of UHF signals by incontinence moisture in the non-contacting moisture sensor wireless embodiment;

an amplitude of said return signal being a function of absorption of UHF signals by moisture irrespective of contact with moisture by said UHF RFID tag;

said UHF RFID tag module further comprising a programmable memory, a microprocessor coupled for writing predetermined ID data into the programmable memory;

said UHF RFID tag returns a condition-response UHF signal for producing acquired sensor signal in the controller-transceiver;

said controller-transceiver coupled to receive retransmitted return UHF signals indicative of at least an identification previously programmed into the RFID tag;

said controller-transceiver and said UHF RFID tag module comprising components to provide power to communicate across a preselected vector distance.

12. A system according to claim 11 wherein said controller and said RFID tag are coupled to a wired sensor-controller system and wherein moisture sensing comprises sensing changes in inductive/capacitive/resistive electrical characteristics in said wired sensor controller system.

13. A system according to claim 11 wherein said antenna comprises the moisture sensor in a wireless sensor-controller system and wherein moisture sensing comprises sensing changes in antenna impedance.

14. A system according to claim 11 wherein said UHF RFID tag further comprises an RF interface coupling said antenna to said microprocessor and an electrically erasable programmable memory (EEPROM) translating signals between said microprocessor and said RF interface.

15. A system according to claim 14 wherein said EEPROM is coupled for storing the acquired sensor data, said microprocessor communicating with an external controller to provide condition-responsive data and wherein said microprocessor is coupled to said EEPROM to enable response to queries for the condition-responsive data from the external controller.

16. A system according to claim 15 wherein said EEPROM comprises locations for storing identity data uniquely associated with said RFID tag.

17. A system according to claim 16 wherein said microprocessor is coupled to receive and store data indicative of patient care personnel actions and of service history of the sensor module, the data being provided from a controller.

18. A system according to claim 16 wherein said sensor module further comprises condition-responsive sensors for sensing parameters other than moisture.

19. A system according to claim 18 wherein said microprocessor further comprises a read only memory (ROM) storing programmed instructions for operating the sensor module.

20. A system according to claim 19 further comprising a controller-transceiver including the external controller and a transceiver communicating with said sensor module and transmitting a signal at a resonant frequency of said antenna.

21. A system according to claim 16 wherein said UHF RFID tag is passive and further comprising a controller-transceiver comprising a controller and a transceiver for transmitting a signal for powering the UHF RFID tag.

22. A system according to claim 21 wherein said controller is programmable to provide information to and read information from said sensor module.

* * * * *